US010501788B2

(12) United States Patent
Chu et al.

(10) Patent No.: US 10,501,788 B2
(45) Date of Patent: Dec. 10, 2019

(54) SYSTEM AND METHODS FOR CALIBRATING BINDING DYES

(71) Applicant: LIFE TECHNOLOGIES CORPORATION, Carlsbad, CA (US)

(72) Inventors: Yong Chu, Castro Valley, CA (US); Jacob Freudenthal, San Jose, CA (US); Jeffrey Marks, Mountain View, CA (US)

(73) Assignee: Life Technologies Corporation, Carlsbad, CA (US)

( * ) Notice: Subject to any disclaimer, the term of this patent is extended or adjusted under 35 U.S.C. 154(b) by 528 days.

(21) Appl. No.: 15/017,034

(22) Filed: Feb. 5, 2016

(65) Prior Publication Data

US 2016/0230209 A1 Aug. 11, 2016

Related U.S. Application Data

(60) Provisional application No. 62/113,118, filed on Feb. 6, 2015.

(51) Int. Cl.
| G01N 33/48 | (2006.01) |
| C12Q 1/686 | (2018.01) |
| G01N 21/27 | (2006.01) |
| G01N 21/64 | (2006.01) |
| G06G 7/58 | (2006.01) |

(52) U.S. Cl.
CPC ........... *C12Q 1/686* (2013.01); *G01N 21/274* (2013.01); *G01N 21/6428* (2013.01); *G01N 21/6452* (2013.01); *G01N 21/6456* (2013.01); *G01N 2021/6421* (2013.01); *G01N 2021/6441* (2013.01); *G01N 2201/127* (2013.01)

(58) Field of Classification Search
None
See application file for complete search history.

(56) References Cited

U.S. PATENT DOCUMENTS

| 7,663,750 B2 | 2/2010 | Bahatt et al. |
| 2007/0100569 A1 | 5/2007 | DeSimas et al. |
| 2008/0001099 A1 | 1/2008 | Sharaf et al. |
| 2008/0178653 A1 | 7/2008 | Gunstream |

FOREIGN PATENT DOCUMENTS

WO 2008003053 A2 1/2008

OTHER PUBLICATIONS

International Search Report and Written Opinion issued in International Application No. PCT/US2016/016817, dated Jun. 14, 2016, 15 pages.
Written Opinion issued in Singapore Application No. 11201706352Q, dated May 24, 2018, pp. 1-5.
Applied Biosystems StepOne(TM) and StepOnePlus(TM) Real-Time PCR Systems, Installation, Networking, and Maintenance Guide, Revision H, Feb. 2016, 192 pages.
Thermal Cycler Spectral Calibration Instructions, CAL Fluor(R) and Quasar(R) Dyes, Biosearch Technologies, Chemistry for Genomics and Proteomics, 2014, pp. 1-22.
iQ5 Calibration Procedure Jun. 2, 2005. v1.3, Bio-Rad Laboratories, pp. 1-19.

*Primary Examiner* — Eric S Dejong
(74) *Attorney, Agent, or Firm* — Mauriel Kapouytian Woods LLP; Lana Akopyan; Michael Mauriel

(57) ABSTRACT

Some embodiments describe a computer-implemented method for calibrating a fluorescent dye. The method can comprise imaging a sample holder, loaded into an instrument, at more than one channel. The sample holder can comprise a plurality of reaction sites and more than one dye type, with each dye occupying more than one reaction site. The method can further comprise identifying a peak channel for each dye on the sample holder, normalizing each channel to the peak channel for each dye, and producing a dye matrix that can comprise a set of dye reference values.

20 Claims, 11 Drawing Sheets

US 10,501,788 B2

SYSTEM AND METHODS FOR CALIBRATING BINDING DYES

FIELD OF THE DISCLOSURE

The present disclosure is directed to biological analysis such as, for example, a polymerase chain reaction (PCR), and biological analysis devices such as, for example, instruments for PCR, especially to dye calibration plates and computer systems and computer software relating to methods for calibration dyes using dye calibration plates.

BACKGROUND

Generally, there is an increasing need to simplify the installation and setup of biological analysis systems so that operators can more quickly and efficiently use biological analysis systems for their intended purpose. For example, advances in the calibration of biological analysis instruments advantageously allow for reduced operator error, reduced operator input, and reduced time necessary to calibrate a biological analysis instrument, and its various components, for proper and efficient installation.

SUMMARY OF THE DISCLOSURE

The present disclosure relates, in some embodiments, to a computer-implemented method for calibrating a fluorescent dye. The method can comprise imaging a sample holder, loaded into an instrument, at more than one channel. The sample holder can comprise a plurality of reaction sites and more than one dye type, with each dye occupying more than one reaction site. The method can further comprise identifying a peak channel for each dye on the sample holder, normalizing each channel to the peak channel for each dye, and producing a dye matrix that can comprise a set of dye reference values. The dye matrix can comprise a set of dye reference values for each reaction site.

In an embodiment, a non-transitory computer-readable storage medium encoded with instructions, executable by a processor, can be provided. The instructions can comprise instructions for imaging a sample holder, loaded into an instrument, at more than one channel. The sample holder can comprise a plurality of reaction sites and more than one dye type, with each dye occupying more than one reaction site. The instructions can further comprise instructions for identifying a peak channel for each dye on the sample holder, normalizing each channel to the peak channel for each dye, and producing a dye matrix that can comprise a set of dye reference values. The dye matrix can comprise a set of dye reference values for each reaction site.

In another embodiment, a system for calibrating a fluorescent dye is provided. The system can comprise a processor and a memory encoded with instructions, executable by the processor. The instructions can comprise instructions for imaging a sample holder, loaded into an instrument, at more than one channel. The sample holder can comprise a plurality of reaction sites and more than one dye type, with each dye occupying more than one reaction site. The instructions can further comprise instructions for identifying a peak channel for each dye on the sample holder, normalizing each channel to the peak channel for each dye, and producing a dye matrix that can comprise a set of dye reference values. The dye matrix can comprise a set of dye reference values for each reaction site.

In a further embodiment, a sample holder for calibrating fluorescent dyes is provided. The sample holder can comprise a plurality of reaction sites. Each of the plurality of reaction sites can be configured to accept a single dye. The sample holder can be configured to accept more than one dye. Alternatively, the sample holder can be a plate. Also, the plurality of reactions sites can be a plurality of wells.

DETAILED DESCRIPTION OF THE EMBODIMENTS

Figure 1:
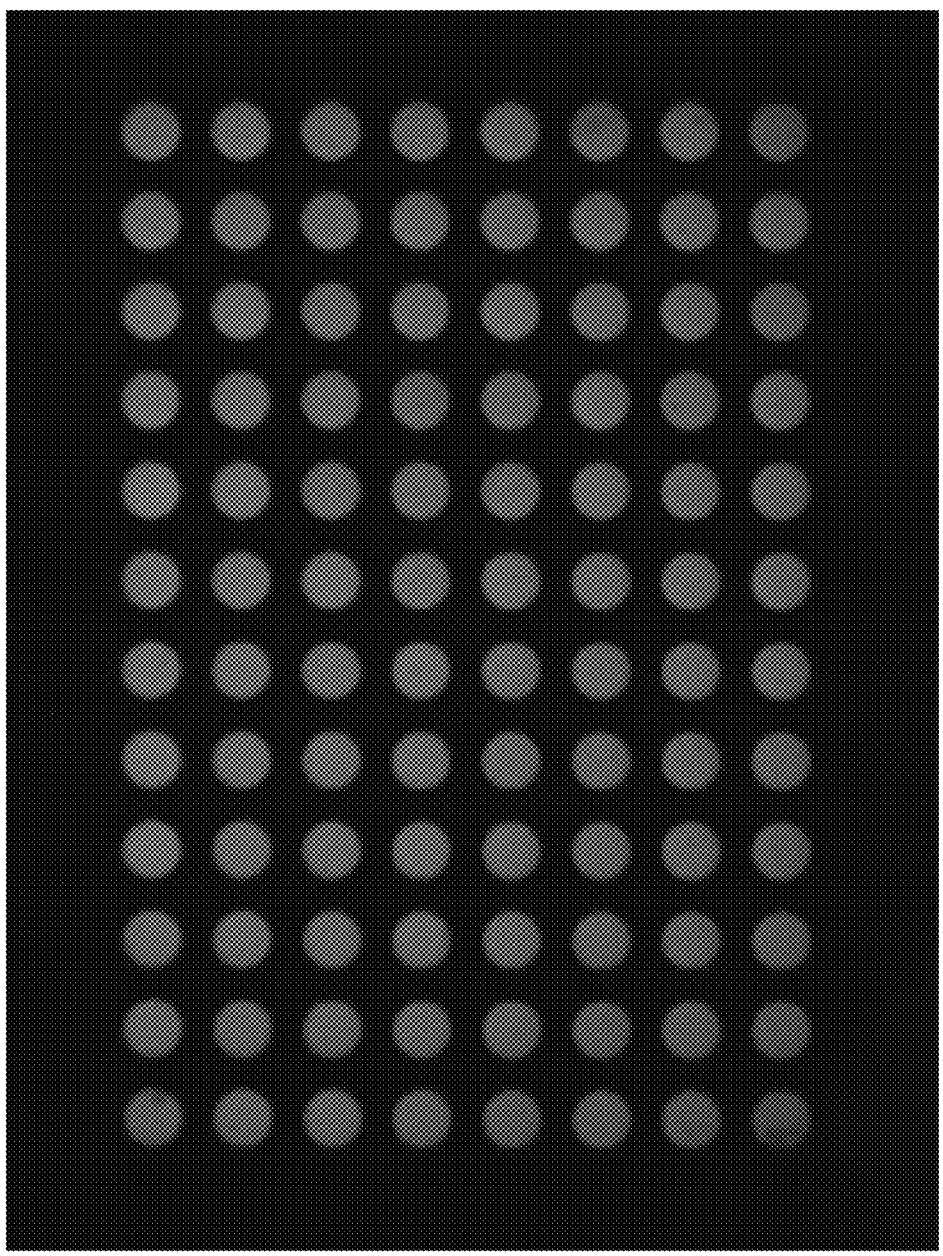
FIG. 1 is an image of a calibration plate with FAM dye occupying each well of a 96-well calibration plate.

To provide a more thorough understanding of the present invention, the following description sets forth numerous specific details, such as specific configurations, parameters, examples, and the like. It should be recognized, however, that such description is not intended as a limitation on the scope of the present invention, but is intended to provide a better description of the exemplary embodiments.

It should also be recognized that the methods and systems described herein may be implemented in various types of systems, instruments, and machines such as biological analysis systems. For example, various embodiments may be implemented in an instrument, system or machine that performs polymerase chain reactions (PCR) on a plurality of samples. While generally applicable to quantitative polymerase chain reactions (qPCR) where a large number of samples are being processed, it should be recognized that any suitable PCR method may be used in accordance with various embodiments described herein. Suitable PCR methods include, but are not limited to, digital PCR, allele-specific PCR, asymmetric PCR, ligation-mediated PCR, multiplex PCR, nested PCR, qPCR, genome walking, and bridge PCR, for example. Furthermore, as used herein, thermal cycling may include using a thermal cycler, isothermal amplification, thermal convection, infrared mediated thermal cycling, or helicase dependent amplification.

As described above, there is an increasing need to simplify the installation and setup of biological analysis systems so that operators can more quickly and efficiently use biological analysis systems for their intended purpose. This need is evident in, for example, calibrating a biological analysis instrument and associated components. One exemplary calibration is the calibrating of fluorescent dyes used for fluorescence detection in biological analysis systems such as, for example, qPCR systems.

Calibrating fluorescent dyes used in a qPCR instrument allows the instrument software to use the calibration data collected from dye standards to characterize and distinguish the individual contribution of each dye in the total fluorescence collected by the instrument. After a sample run, the instrument software receives data in the form of a raw spectra signal for each reading. The software determines the contribution of each of the fluorescent dyes used in each reaction site by comparing the raw spectra, contributed by each dye, to the pure spectra calibration data. When a user saves an experiment after analysis, the instrument software stores the pure spectra along with the collected fluorescence data for that experiment, as well as the contribution of each fluorescence dye per well.

The product of a dye calibration in a qPCR instrument, for example, is a collection of spectral profiles that represent the fluorescence signature of each dye standard for each reaction site. Each profile consists of a set of spectra that correspond to the fluorescence collected from reaction sites, such as wells, of a sample holder such as, for example, a calibration plate or array card. Following the calibration of each dye, the instrument software "extracts" a spectral profile for each dye at each reaction site. The software plots the resulting data for each profile in a graph of fluorescence versus filter. When the software extracts the dye calibration data, it evaluates the fluorescence signal generated by each well in terms of the collective spectra for the entire calibration plate or array card. Dye spectra are generally acceptable if they peak within the same filter as their group, but diverge slightly at other wavelengths.

When running dye calibration on a sample holder, such as a calibration plate, the reaction sites (e.g., wells) generally contain identical concentrations of dye to allow generation of a pure spectra value at each well of the plate. FIG. 1 displays an image of a calibration plate with a single dye (in this case, FAM dye), occupying each well of a 96-well calibration plate. This allows for the comparison of fluorescence signal generated by each well in a run to a pure spectra read for that well. By using a single dye for each well of a calibration plate, the resulting signals for the wells should be similar. Variations in spectral position and peak position can be caused, for example, by minor differences in the optical properties and excitation energy between the individual wells. Taking these variations into account in dye calibration theoretically leads to a more accurate dye calibration.

However, the use of a single dye per calibration plate could be time intensive and complicated, particularly when calibrating numerous dyes. Non-limiting examples of fluorescent dyes include FAM, VIC, ROX, SYBR, MP, ABY, JUN, NED, TAMRA and CY5. Therefore, a need exists to simplify the dye calibration process and reduce the time required for calibration while maintaining the same quality of results of the dye calibration.

Computer-Implemented System

Methods of dye calibration in accordance with embodiments described herein may be implemented in a computer system.

Those skilled in the art will recognize that the operations of the various embodiments may be implemented using hardware, software, firmware, or combinations thereof, as appropriate. For example, some processes can be carried out using processors or other digital circuitry under the control of software, firmware, or hard-wired logic. (The term "logic" herein refers to fixed hardware, programmable logic and/or an appropriate combination thereof, as would be recognized by one skilled in the art to carry out the recited functions.) Software and firmware can be stored on non-transitory computer-readable media. Some other processes can be implemented using analog circuitry, as is well known to one of ordinary skill in the art. Additionally, memory or other storage, as well as communication components, may be employed in embodiments of the invention.

Figure 2:
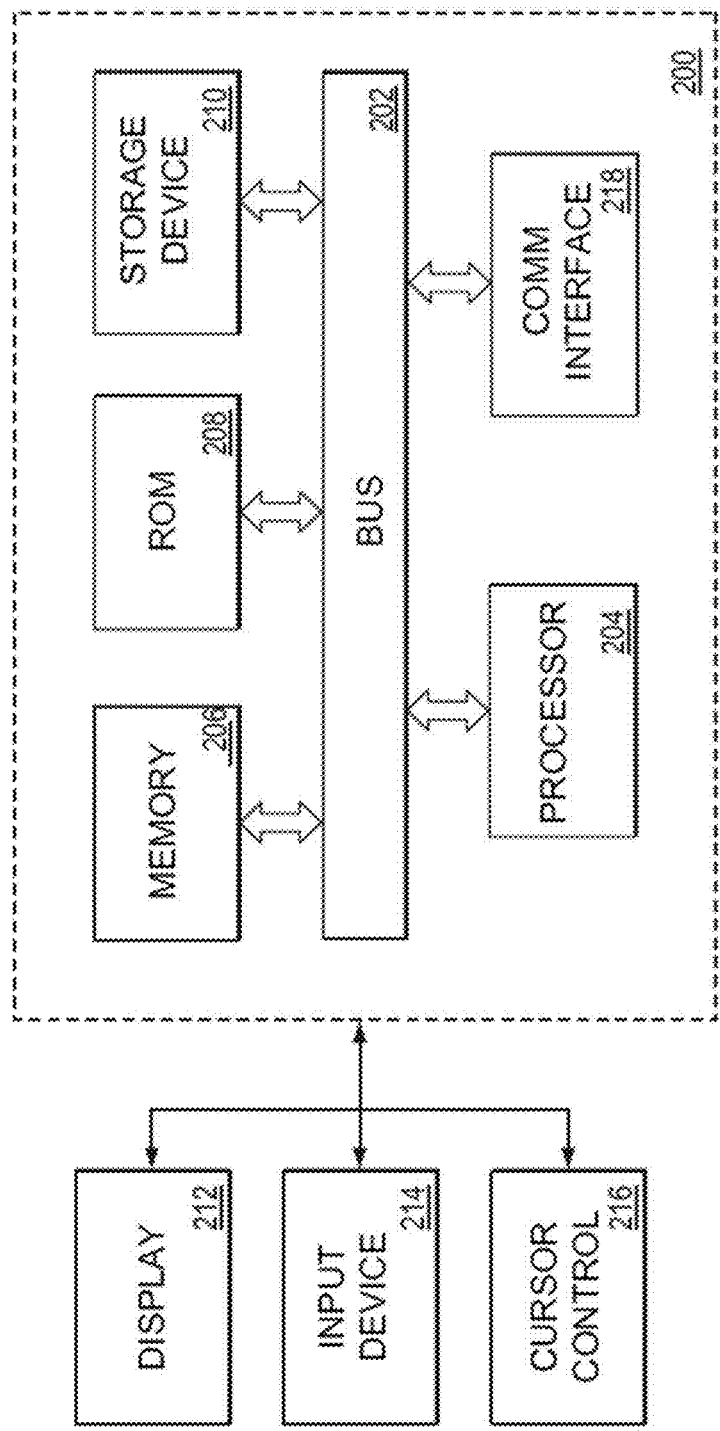
FIG. 2 is a block diagram that illustrates a computer system 200 that may be employed to carry out processing functionality, according to some exemplary embodiments of the disclosure.

FIG. 2 is a block diagram that illustrates a computer system 200 that may be employed to carry out processing functionality, according to various embodiments. Instruments to perform experiments may be connected to the exemplary computing system 200. According to various embodiments, the instruments that may be utilized include, for example, thermal cycler system 300 of FIG. 3 discussed in more detail below. Computing system 200 can include one or more processors, such as a processor 204. Processor 204 can be implemented using a general or special purpose processing engine such as, for example, a microprocessor, controller or other control logic. In this example, processor 204 is connected to a bus 202 or other communication medium.

Further, it should be appreciated that a computing system 200 of FIG. 2 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 200 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks are well documented in the art. According to various embodiments described herein, computing system 200 may be configured to connect to one or more servers in a distributed network. Computing system 200 may receive information or updates from the distributed network. Computing system 200 may also transmit information to be stored within the distributed network that may be accessed by other clients connected to the distributed network.

Computing system 200 may include bus 202 or other communication mechanism for communicating information, and processor 204 coupled with bus 202 for processing information.

Computing system 200 also includes a memory 206, which can be a random access memory (RAM) or other dynamic memory, coupled to bus 202 for storing instructions to be executed by processor 204. Memory 206 also may be used for storing temporary variables or other intermediate information during execution of instructions to be executed by processor 204. Computing system 200 further includes a read only memory (ROM) 208 or other static storage device coupled to bus 202 for storing static information and instructions for processor 204.

Computing system 200 may also include a storage device 210, such as a magnetic disk, optical disk, or solid state drive (SSD) is provided and coupled to bus 202 for storing information and instructions. Storage device 210 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 210 may include other similar instrumentalities for allowing computer programs or other instructions or data to be loaded into computing system 200. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 210 to computing system 200.

Computing system 200 can also include a communications interface 218. Communications interface 218 can be used to allow software and data to be transferred between computing system 200 and external devices. Examples of communications interface 218 can include a modem, a network interface (such as an Ethernet or other NIC card), a communications port (such as for example, a USB port, a RS-232C serial port), a PCMCIA slot and card, Bluetooth, etc. Software and data transferred via communications interface 218 are in the form of signals which can be electronic, electromagnetic, optical and/or other signals capable of being received by communications interface 218. These signals may be transmitted and received by communications interface 218 via a channel such as a wireless medium, wire or cable, fiber optics, or other communications medium. Some examples of a channel include a phone line, a cellular phone link, an RF link, a network interface, a local or wide area network, and other communications channels.

Computing system 200 may be coupled via bus 202 to a display 212, such as a cathode ray tube (CRT) or liquid crystal display (LCD), for displaying information to a computer user. An input device 214, including alphanumeric and other keys, is coupled to bus 202 for communicating information and command selections to processor 204, for example. An input device may also be a display, such as an LCD display, configured with touchscreen input capabilities. Another type of user input device is cursor control 216, such as a mouse, a trackball or cursor direction keys for communicating direction information and command selections to processor 204 and for controlling cursor movement on display 212. This input device typically has two degrees of freedom in two axes, a first axis (e.g., x) and a second axis (e.g., y), that allows the device to specify positions in a plane. A computing system 200 provides data processing and provides a level of confidence for such data. Consistent with certain implementations of embodiments of the present teachings, data processing and confidence values are provided by computing system 200 in response to processor 204 executing one or more sequences of one or more instructions contained in memory 206. Such instructions may be read into memory 206 from another computer-readable medium, such as storage device 210. Execution of the sequences of instructions contained in memory 206 causes processor 204 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 204 for execution. Such instructions, generally referred to as "computer program code" (which may be grouped in the form of computer programs or other groupings), when executed, enable the computing system 200 to perform features or functions of embodiments of the present invention. These and other forms of non-transitory computer-readable media may take many forms, including but not limited to, non-volatile media, volatile media, and transmission media. Non-volatile media includes, for example, solid state, optical or magnetic disks, such as storage device 210. Volatile media includes dynamic memory, such as memory 206. Transmission media includes coaxial cables, copper wire, and fiber optics, including the wires that comprise bus 202.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 204 for execution. For example, the instructions may initially be carried on magnetic disk of a remote computer. The remote computer can load the instructions into its dynamic memory and send the instructions over a telephone line using a modem. A modem local to computing system 200 can receive the data on the telephone line and use an infra-red transmitter to convert the data to an infra-red signal. An infra-red detector coupled to bus 202 can receive the data carried in the infra-red signal and place the data on bus 202. Bus 202 carries the data to memory 206, from which processor 204 retrieves and executes the instructions. The instructions received by memory 206 may optionally be stored on storage device 210 either before or after execution by processor 204.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

PCR Instruments

Figure 3:
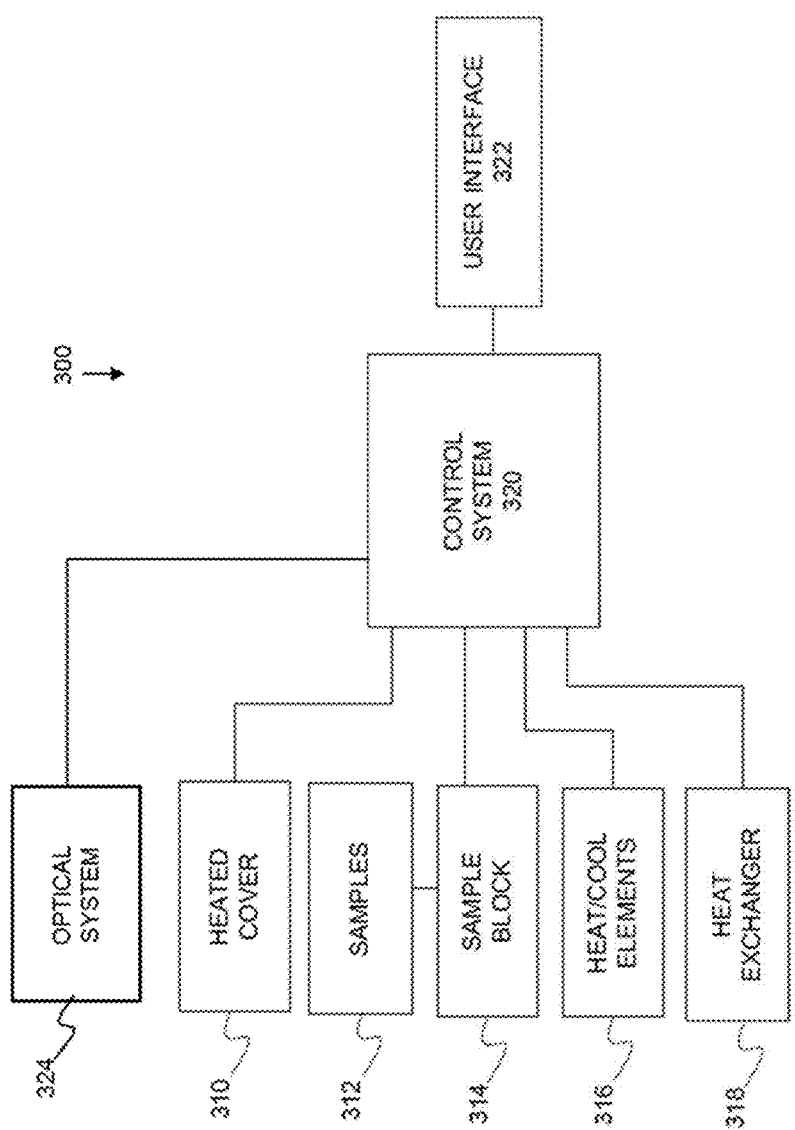
FIG. 3 is a block diagram that illustrates a PCR instrument 300 upon which embodiments of the present teachings may be implemented.

As mentioned above, an instrument that may be utilized according to various embodiments, but is not limited to, is a polymerase chain reaction (PCR) instrument. FIG. 3 is a block diagram that illustrates a PCR instrument 300, upon which embodiments of the present teachings may be implemented. PCR instrument 300 may include a heated cover 310 that is placed over a plurality of samples 312 contained in a substrate (not shown). In various embodiments, a substrate may be a glass or plastic slide with a plurality of sample regions, which sample regions have a cover between the sample regions and heated cover 310. Some examples of a substrate may include, but are not limited to, a multi-well plate, such as a standard microtiter 96-well, a 384-well plate, or a microcard, or a substantially planar support, such as a glass or plastic slide. The reaction sites in various embodiments of a substrate may include depressions, indentations, ridges, and combinations thereof, patterned in regular or irregular arrays formed on the surface of the substrate. Various embodiments of PCR instruments include a sample block 314, elements for heating and cooling 316, a heat exchanger 318, control system 320, and user interface 322. Various embodiments of a thermal block assembly according to the present teachings comprise components 314-318 of PCR instrument 300 of FIG. 3.

Real-time PCR instrument 300 has an optical system 324. In FIG. 3, an optical system 324 may have an illumination source (not shown) that emits electromagnetic energy, an optical sensor, detector, or imager (not shown), for receiving electromagnetic energy from samples 312 in a substrate, and optics 340 used to guide the electromagnetic energy from each DNA sample to the imager. For embodiments of PCR instrument 300 in FIG. 3 and real-time PCR instrument 300 in FIG. 3, control system 320, may be used to control the functions of the detection system, heated cover, and thermal block assembly. Control system 320 may be accessible to an end user through user interface 322 of PCR instrument 300 in FIG. 3 and real-time PCR instrument 300 in FIG. 3. Also a computer system 200, as depicted in FIG. 2, may serve as to provide the control the function of PCR instrument 300 in FIG. 3, as well as the user interface function. Additionally, computer system 200 of FIG. 2 may provide data processing, display and report preparation functions. All such instrument control functions may be dedicated locally to the PCR instrument, or computer system 200 of FIG. 2 may provide remote control of part or all of the control, analysis, and reporting functions, as will be discussed in more detail subsequently.

Opticdal System for Imaging

Figure 4:
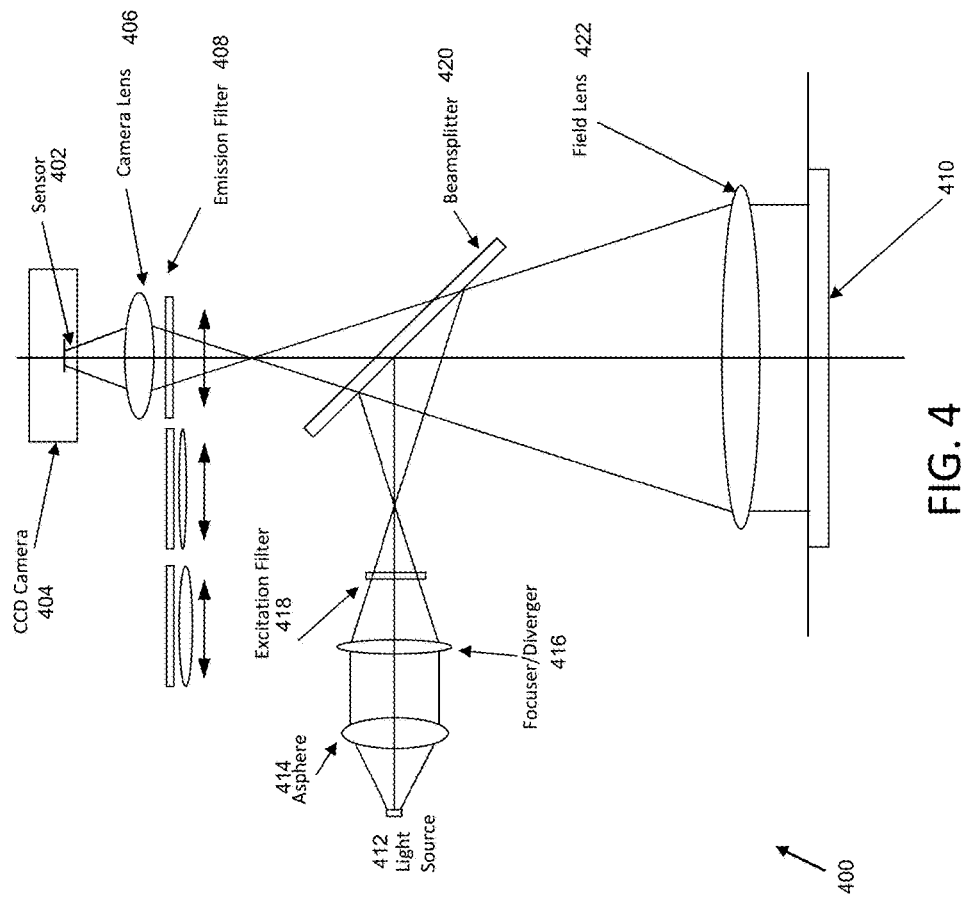
FIG. 4 depicts an exemplary optical system 400 that may be used for imaging according to embodiments described herein.

FIG. 4 depicts an exemplary optical system 400 that may be used for imaging according to embodiments described herein. It should be recognized that optical system 400 is an exemplary optical system and one skilled in the art would recognize that other optical systems may be used to capture images an object-of-interest. According to various embodiments, an object of interest may be a sample holder such as, for example, a calibration plate as described herein. An optical sensor 402 included in a camera 404, for example, may image an object-of-interest 410. The optical sensor 402 may be a CCD sensor and the camera 404 may be a CCD camera. Further, the optical sensor includes a camera lens 406.

Depending on the object of interest, an emission filter 408 can be chosen for imagining the object-of-interest 410 according to various embodiments. Emission filter 408 may be changed to image fluorescent emission emitted from the object-of-interest 401 in other embodiments.

Optical system 400 may use a reflected light source 412 to image object-of-interest 410. The light from light source 412 may be filtered through an asphere 414, a focuser/diverger 416, and excitation filter 418 before being reflected to the object-of-interest 410 by beamsplitter 420. Optical system 400 may also include a field lens 422. Depending on the object of interest, the excitation filter 418 can be chosen or changed for imagining the object-of-interest 410 according to various embodiments.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Improved Workflow and Plate for Calibrating Fluorescence Dyes

Figure 5:
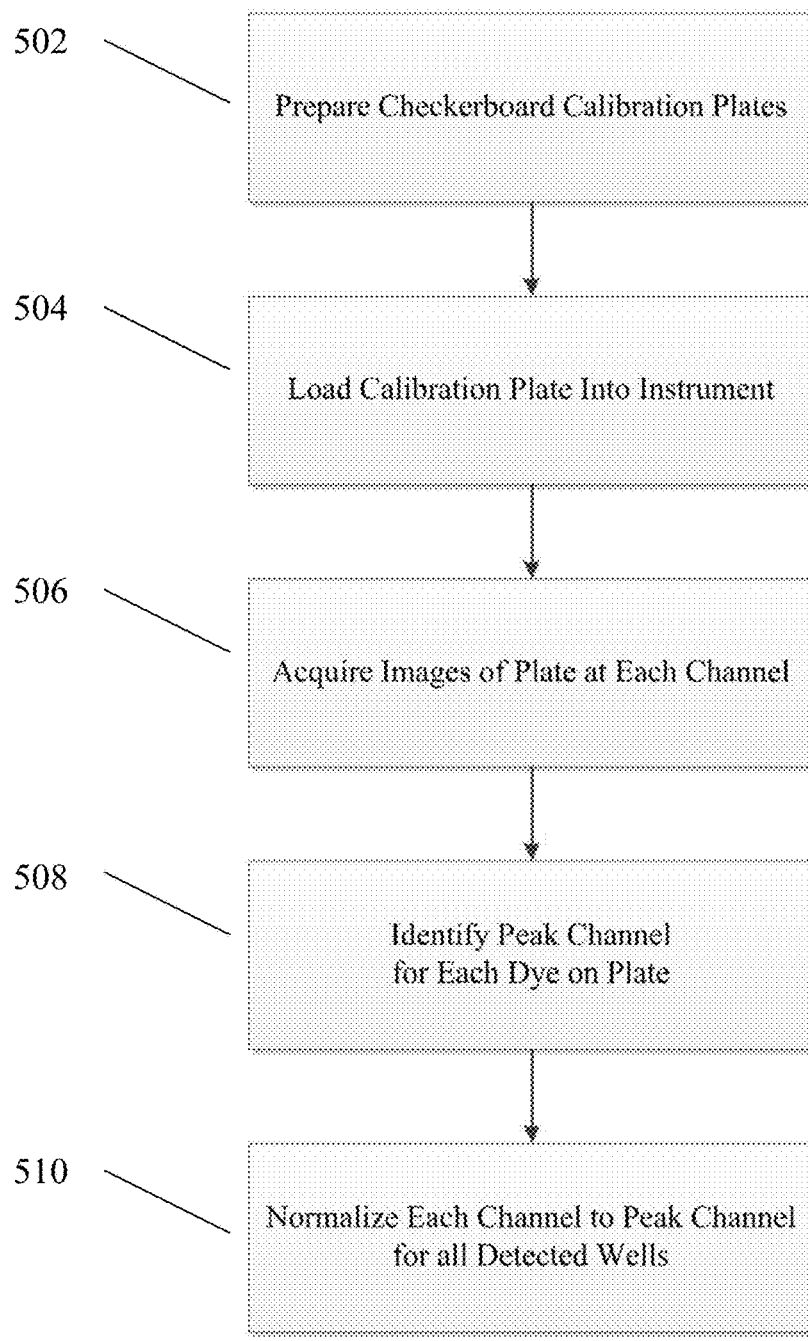
FIGS. 5 and 6 depict an example workflow according to an embodiment of the present disclosure.
Figure 6:
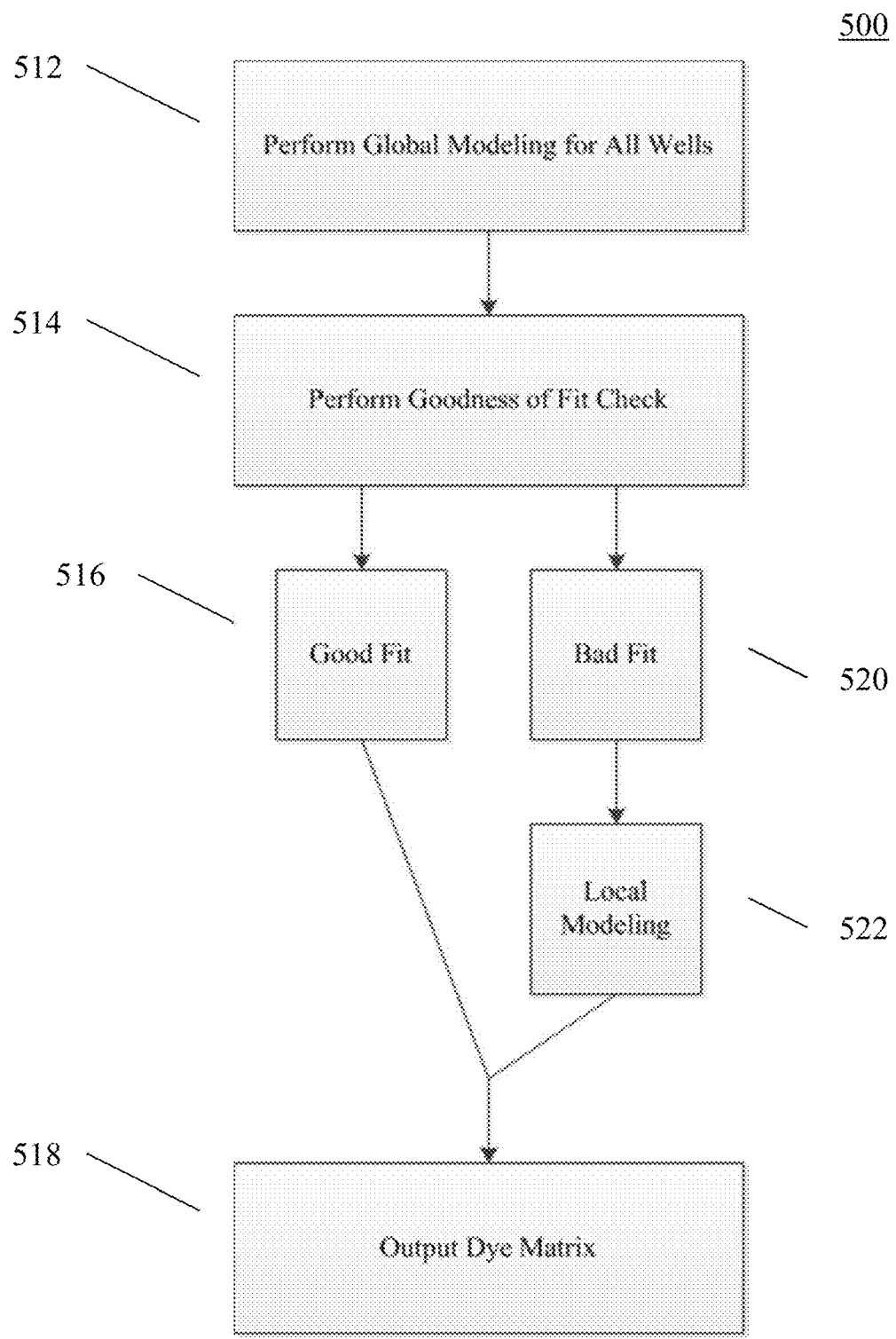

FIGS. 5 and 6 illustrate a flowchart depicting an exemplary method 500 of calibrating fluorescent dye(s) according to embodiments described herein. The steps of method 500 may be implemented by a processor 204, as shown in FIG. 2. Furthermore, instructions for executing the method by processor 204 may be stored in memory 206.

With reference to FIG. 5, in step 502, calibration plates are prepared by loading dyes into reaction sites of a substrate for processing. The substrate, in this case, is a 96-well plate, though different substrates may be used including, for example, a 384-well plate. In various embodiments, the substrate may be a glass or plastic slide with a plurality of sample regions. Some examples of a substrate may include, but are not limited to, a multi-well plate, such as a standard microtiter 96-well plate, a 384-well plate, or a microcard, a substantially planar support, such as a glass or plastic slide, or any other type of array or microarray. The reaction sites in various embodiments of a substrate may include wells, depressions, indentations, ridges, and combinations thereof, patterned in regular or irregular arrays formed on the surface of the substrate. Heretofore, reference to wells or plates are just for exemplary purposes only and not in any way to limit the type of reaction site or sample holder useable herein.

Figure 7A:
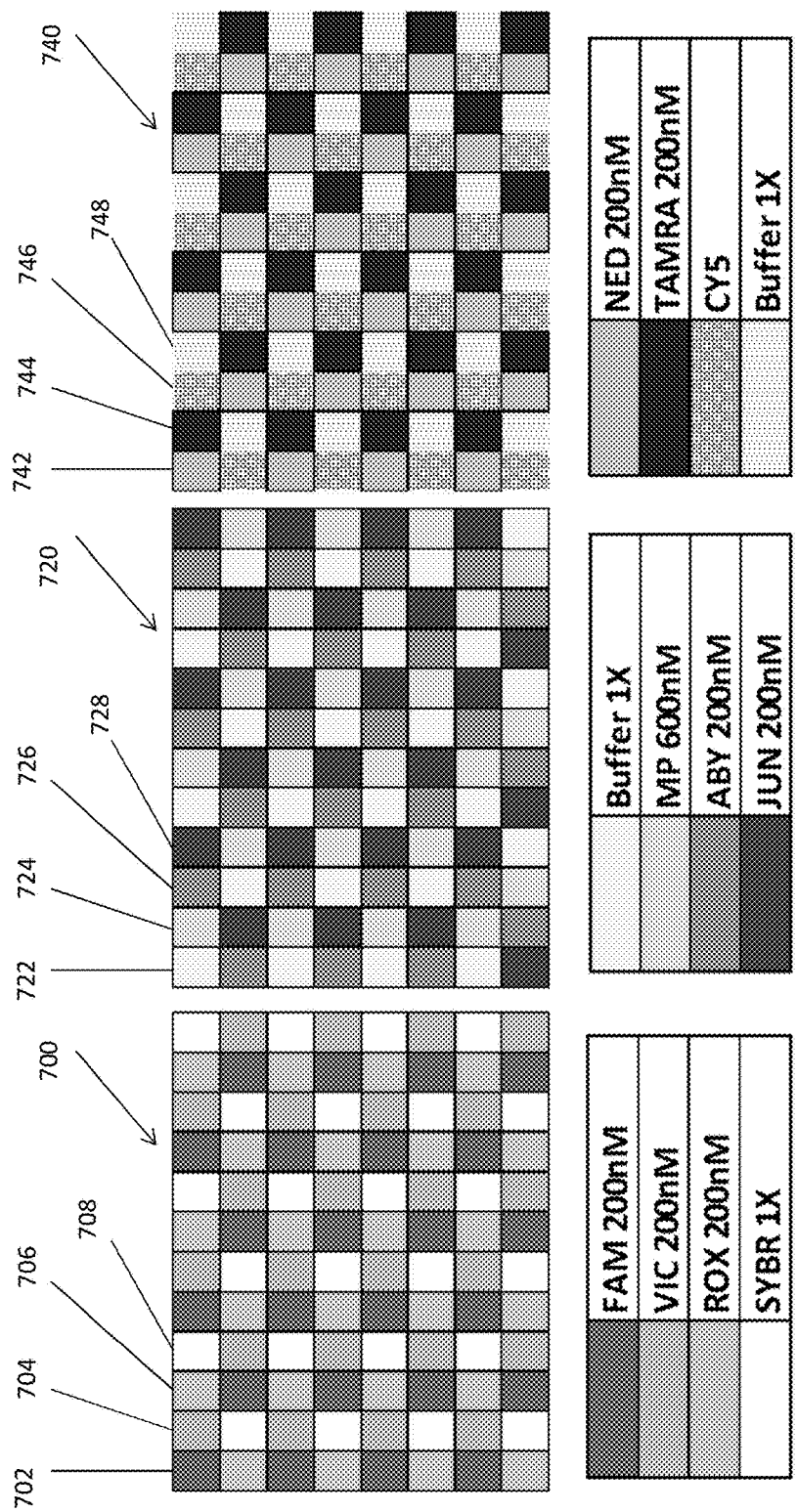
FIG. 7A illustrates calibration plates with checkerboard configurations according to an embodiment of the present disclosure.
Figure 10:
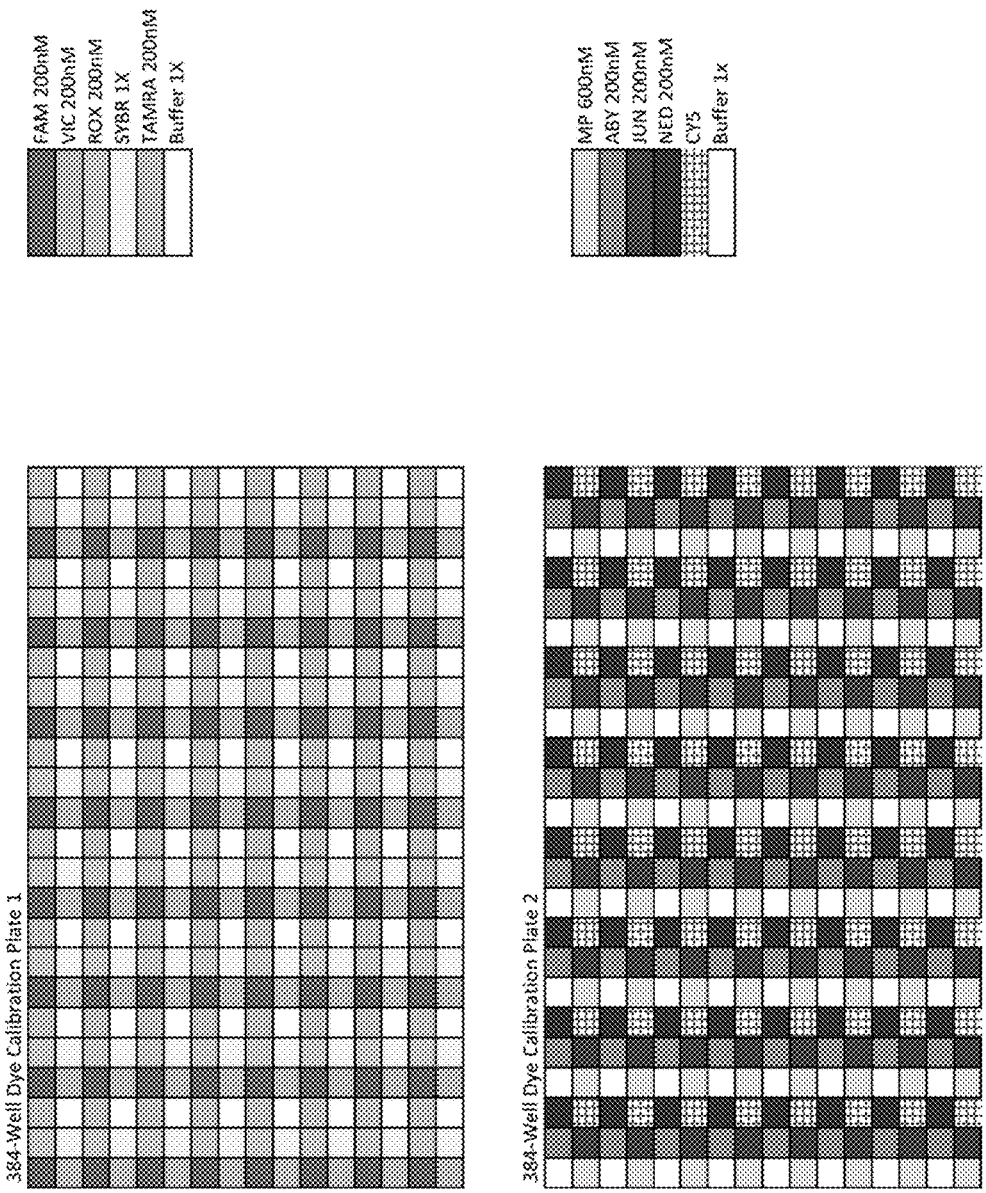
FIG. 10 illustrates calibration plates with checkerboard configurations according to an embodiment of the present disclosure.

The calibration plates may be prepared in a checkerboard pattern as illustrated in FIG. 7A (or FIG. 10 for a 384-well plate, discussed in more detail below). As illustrated in calibration plates 700, 720 and 740, the plates themselves may be of a 96-well format, though the number of wells on the calibration plate can be varied as needed depending on, for example, the number of dyes requiring calibration, the sample block 314 (see FIG. 3) format accepting the calibration plate, or the capabilities of the instrument (PCR instrument 300 for example) to image plates of different well densities.

The checkerboard pattern of dye distribution allows multiple dyes to be calibrated per calibration plate. As opposed to calibrating one dye per calibration plate, the checkerboard pattern advantageously allows a user to use fewer plates to calibrate a dye set, thus decreasing time and process steps needed for dye calibration.

In the embodiment illustrated in FIG. 7A, three plates are used to calibrate ten separate dyes. Each calibration plate 700/720/740 is configured to accommodate four different dyes in a repeating pattern of alternating dyes along wells in each row of the plate such that each well presents a specific dye in the repeating pattern (dye presented well). For example, plate 700 accommodates FAM, VIC, ROX and SYBR dyes in alternating wells exemplified by wells 702 (FAM), 704 (VIC), 706 (ROX) and 708 (SYBR); plate 720 accommodates a buffer, MP dye, ABY dye and JUN dye in alternating wells exemplified by wells 722 (buffer), 724 (MP), 726 (ABY) and 728 (JUN); and plate 740 accommodates NED dye, TAMRA dye, CY5 dye and a buffer in alternating wells exemplified by wells 742 (NED), 744 (TAMRA), 746 (CY5) and 748 (buffer). In this embodiment, since only ten dyes are being calibrated, buffers are used in plates 720 and 740 as filler for wells not accommodating a dye to be calibrated.

Figure 7B:
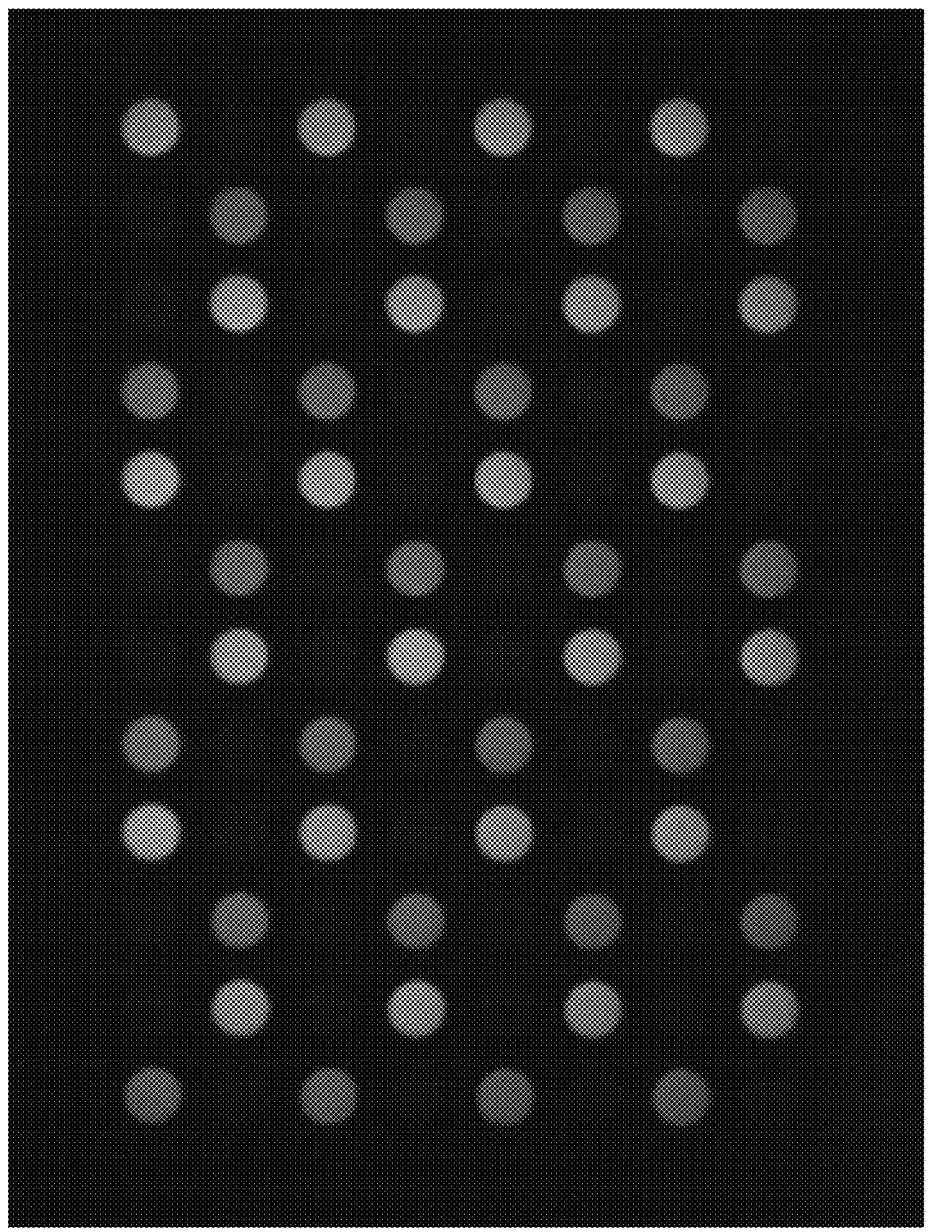
FIG. 7B is an image of a 4 dye checkerboard 96-well calibration plate with FAM, VIC, ROX and SYBR dyes in the same configuration as illustrated by plate 700 in FIG. 7A.

It should be appreciated that the embodiment in FIGS. 7A and 7B is an example only, and that the number of total dyes calibrated, the number of dyes per plate, and the number of plates, can all vary as needed based, for example, on a user's calibration needs, the number of wells on the plate, and capacity of the instrument handling the calibration. For example, if 12 dyes were being calibrated in the embodiment illustrated in FIG. 7A, a buffer would not be needed in plates 720 and 740, as four dyes could be calibrated in each of the three calibration plates 700/720/740 for a total of 12 dyes.

Moreover, the number of dyes per plate can be two or more, with the maximum number of dyes per plate based on, for example, the number of wells on the calibration plate, the capability of the instrument used to properly model a full plate (see below for further explanation), and the capability of the imaging system to obtain usable fluorescence data from the plate chosen. For example, rather than using a 96-well plate as illustrated in FIG. 7A, one may have a sufficiently robust instrument and associated imaging system to be able to use a 384-well calibration plate as provided in FIG. 10. With the additional well density provided, one could calibrate more dyes per plate, for example 16 dyes per plate, and still get the same number of data points (i.e., dye presented wells) per dye (e.g., 24) needed to get a sufficient global model (discussed in more detail below). In FIG. 10, for example, 10 dyes can be calibrated using two plates and five dyes per plate.

Even the type of sample holder and type of reaction site may affect the number of dyes possible. As stated above, other types of sample holders and reaction sites may be used for calibration.

Returning to FIG. 5, in step 504, prepared checkerboard calibration plates can be loaded into the instrument. The number of plates loadable into an instrument at one time depends on the capabilities and capacity of the instrument used. For example, a standard qPCR thermal cycler with a 96-well block will only accept on calibration plate at a time. However, multi-block thermal cyclers may offer multiple blocks that can each accept a calibration plate. Moreover, if a calibration plate is not used, depending on the format of the sample holder used (e.g., a microarray or microchip array), multiple sample holders may be received in a single instrument using, for example, a loading assembly that fits into the instrument.

In step 506 of FIG. 5, the instrument, using its associated optical imaging system (see, for example, FIG. 4), acquires images of the loaded calibration plate, or plates, in series or parallel. The acquired images and associated data can be stored, for example, on memory 206 or storage device 210 of computing system 200 in FIG. 2. The optical imaging system can acquire images of each plate at each optical channel. The number of channels depends on the number of excitation and emission filters provided in the imaging system. For example, for an optical imaging system having 6 excitation filters (X filters) and 6 emission filters (M filters), the total number of channels is 21, represented by the following filter combinations: X1M1, X1M2, X1M3, X1M4, X1M5, X1M6, X2M2, X2M3, X2M4, X2M5, X2M6, X3M3, X3M4, X3M5, X3M6, X4M4, X4M5, X4M6, X5M5, X5M6, and X6M6. The number of images or exposures acquired at each channel can vary. For example, the imaging system can acquire two images or exposures per channel. The number of images or exposures taken depends on user needs, as taking fewer images or exposures per channel may decrease the time needed to acquire images or exposures, while taking more images or exposures per channel provides greater likelihood of quality data.

In step 508 of FIG. 5, the instrument, using the data gathered from the images or exposures acquired by the optical imaging system (see, for example, FIG. 4), identifies the peak channel for each dye on the calibration plate. This peak channel for each reaction site is the channel where the specific dye analyzed shows the greatest fluorescence for that reaction site. The peak channel identification can occur when, for example, 95% or more reaction sites are dye occupied, in this case allowing no more than 5% outlier reaction sites during calibration. The percentage of allowable outliers can vary. The outlier reaction sites can then be discarded from future calculation and analysis. Outliers can occur, for example, when the wrong dyes are loaded, the dyes are loaded in the incorrect configuration, there is improper loading of dyes, or optical components become dirty (e.g., dust particles). The peak channel for each dye on the calibration plate can be identified, for example, by processor 204, of computing system 200, utilizing data stored on memory 206. The identification results can be stored, for example, on memory 206 or storage device 210 of computing system 200.

Alternatively, the collected fluorescence data gathered from the images or exposures acquired by the optical imaging system for each filter combination on each reaction site can be corrected by background and uniformity correction before peak channel identification, using background component and uniformity factors determined using background and uniformity calibrations methods known in the art.

In step 510 of FIG. 5, the instrument, using the data gathered from the images or exposures acquired by the optical imaging system (see, for example, FIG. 4), normalizes each channel to the identified peak channel of step 508 for all the dye presented wells. Each channel can be normalized to the identified peak channel, for example, by processor 204, of computing system 200, utilizing data stored on memory 206. The results of the normalization can be stored, for example, on memory 206 or storage device 210 of computing system 200.

All dye presented wells are given a baseline quant value from which to normalize from. Generally, the greater the quant value, the greater the detected fluorescence. Therefore, the identified peak channel for a given dye would have the largest quant value for that dye in the dye presented wells, excluding peak channel outliers. Regardless of the quant value in that peak channel, to normalize, that quant value at that channel is reset to a value of one. The remaining quant values for that same dye at the other channels are then adjusted according to the reset value of one for the peak channel. For example, if for dye X, the peak channel A had a quant value of 100 in the wells, and other channel B had a quant value of 40 in the wells, upon normalization, peak channel A gets set to 1.0 and channel B gets set to 0.40. This normalized value can also be referred to as a calibration factor, with the calibration factor for the peak channel being set to 1.0 as discussed above.

In the embodiment illustrated in FIGS. 7A and B, where four dyes are equally dispersed among the wells of a 96-well plate, the number of dye presented wells per dye would be 24. The number of dye presented wells can vary for reasons discussed previously such as, for example, the number of reaction sites (e.g., wells) on the sample holder (e.g., calibration plate), the number of dyes per dispersed on the sample holder. For example, on a 96-well plate, if three dyes are dispersed, the number of dye presented wells would be 32 per dye. If there are six dyes dispersed on the 96-well plate, there would be 16 dye presented wells per dye.

With reference now to FIG. 6, in step 512, the instrument performs global modeling for all wells per dye. In order to calibrate a dye for all wells of a sample holder format, the instrument can use the data from the dye presented wells for a specific dye to model for all wells including the ones without the specific dye. The global modeling can be performed, for example, by processor 204, of computing system 200, by using the data from the dye presented wells for a specific dye to model for all wells. The resulting model can be stored, for example, on memory 206 or storage device 210. Referring to FIG. 7A, for the FAM dye present in 24 wells 702 of plate 700, the other 72 wells on that plate would be FAM dye unpresented. The same 24 presented/72 unpresented distribution would apply to each dye in FIG. 7A. The number of dye unpresented wells depends on the number of dye presented wells, which, as discussed above, can depend for various reasons. Regardless, the sum of dye presented and unpresented wells for a given plate equals the number of wells on that plate. FIG. 7B is an image of a 4 dye checkerboard 96-well calibration plate with FAM, VIC, ROX and SYBR dyes in the same configuration as illustrated by plate 700 in FIG. 7A.

In an alternative embodiment, the instrument performs global modeling for all channels or those channels that have a normalized value, for example, greater than 0.01, or 1% of the identified peak channel. For those channels below this threshold, the instrument would perform a local modeling (see step 522 of FIG. 6) instead of performing global modeling. Global modeling may become unnecessary at such low levels at certain channels such that detected fluorescence is primarily a result of, for example, noise or other disturbance, rather than contribution of the actual dye being calibrated.

A global modeling algorithm can function in a dye calibration to derive a model of dye calibration factors for each filter channel for each dye based on the measured dye calibration factors of the specific dye presented wells. For example, if 24 wells are presented on the 96-well checkerboard plate for a specific dye, global modeling utilizes the dye calibration factors of those 24 wells to derive calibration factors for the all wells including other dye unpresented 72 wells, and thus produce a model for the whole plate per channel, per dye.

The two-dimensional (2D) quadratic polynomial function is an example of a function that can be applied as a global model for dye calibration factors. Other global modeling functions are known and can be used herein. A non-linear least square solver can be used to derive the 2D quadratic polynomial function from the measured dye calibration factors on the specific dye presented wells by minimizing the modeling residuals (the difference between the values calculated from the model and the measured dye calibration factors). Levenberg-Marquardt Trust region algorithm can be used as the optimization algorithm in this solver. While many other optimization algorithms are useable herein, one other example is the Dogleg method, whose key idea is to use both Gauss-Newton and Cauthy methods to calculate the optimization step to optimize the non-linear objective. This approach approximates the objective function using a model function (often a quadratic) over a subset of the search space known as the trust region. If the model function succeeds in minimizing the true objective function, the trust region is expanded. Conversely, if the approximation is poor, then the region is contracted and the model function is applied again. A loss function, for example, may also be used to reduce the influence of the high residuals (greatest difference between calculated and measured calibration factors). These high residuals usually constitute outliers on the optimization.

In step 514 of FIG. 6, after all wells are modeled for a given dye or dyes, the instrument performs a goodness of fit (GOF) check. This can ensure that the global modeling step is sufficiently reliable. A GOF check can be performed, for example, by processor 204 of computing system 200, with the results stored, for example, on memory 206 or storage device 210. Measures of goodness of fit typically summarize the discrepancy between observed values and the values expected under the model in question. GOF can be determined in many ways including, for example, coefficient of determination R-squared and root-mean-square error (RMSE) values. R-squared, for example, is a statistic that will give some information about the goodness of fit of a model. In regression, the R-squared coefficient of determination is a statistical measure of how well the regression line approximates the real data points. An R-squared of 1 indicates that the regression line perfectly fits the data. RMSE is the square root of the mean square of the differences or residuals between observed values and the values expected under the model in question, RMSE is a good measure of the predication accuracy of the model. A RMSE of 0 indicates the values expected under the model are exactly matched to the observed values.

Figure 8:
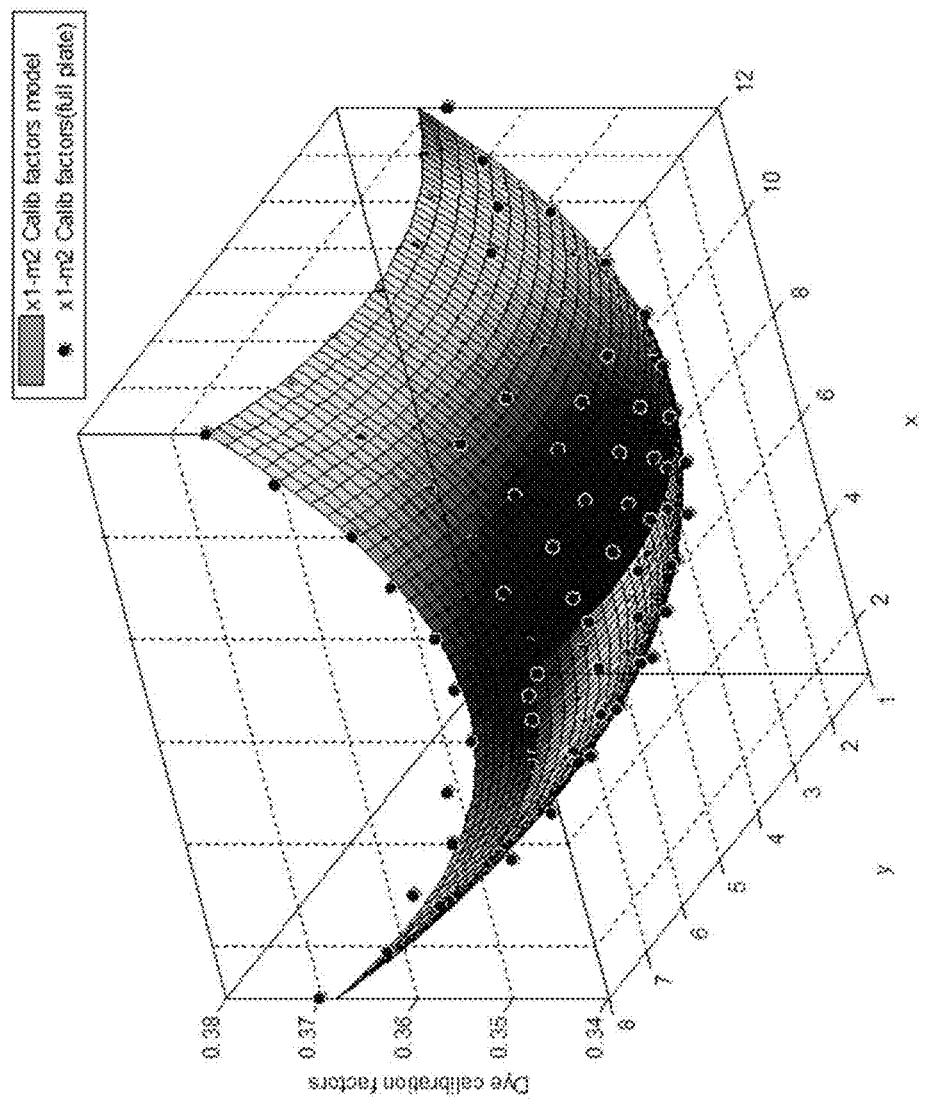
FIG. 8 illustrates an example the 2D quadratic polynomial function applied as a global model for a 96-well checkerboard plate with FAM dye at channel X1M2 according to an embodiment of the present disclosure.
Figure 9:
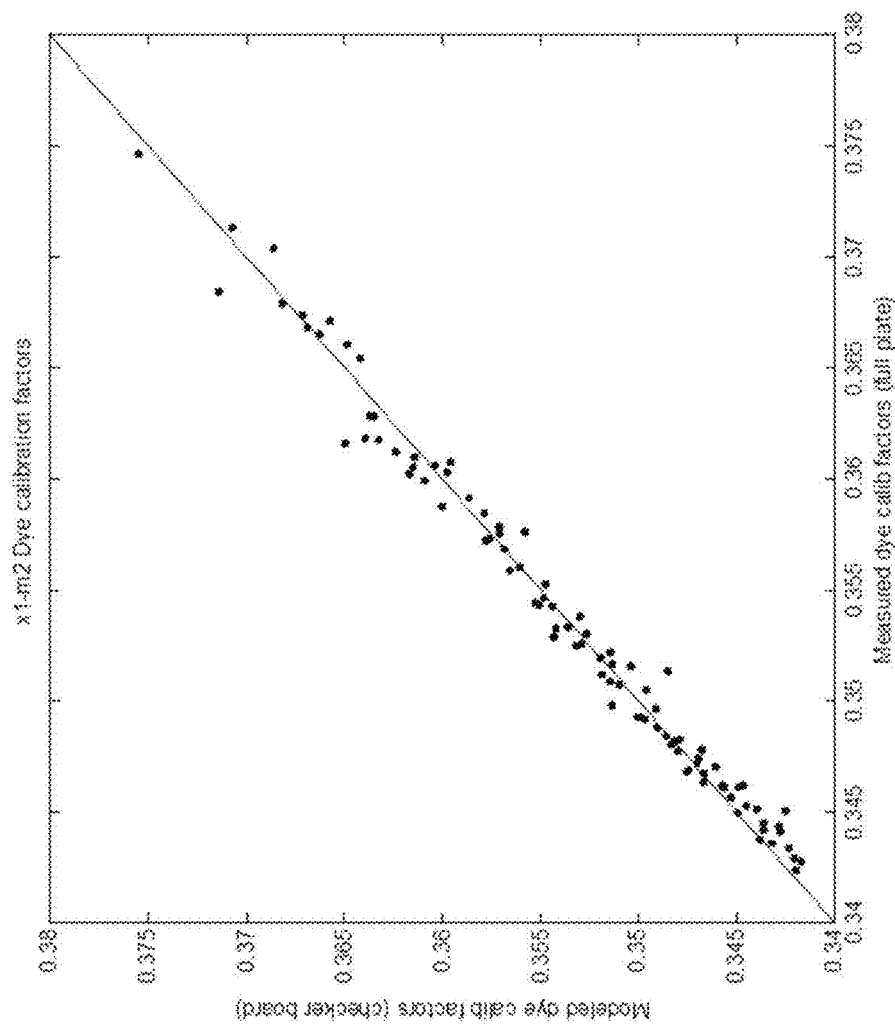
FIG. 9 illustrates a global modeling performance with measured dye calibration factors for a full plate (x-axis) and modeled dye calibration factors for a checkerboard plate (y-axis) according to an embodiment of the present disclosure.

FIG. 8 illustrates an example the 2D quadratic polynomial function applied as a global model for a 96-well checkerboard plate with FAM dye at channel X1M2. For comparison, pure FAM due values from a full dye plate with 96 detected values overlies the model. FIG. 9 provides an illustration of global modeling performance by comparing the measured dye calibration factors for a full plate (x-axis) against the modeled dye calibration factors for a checkerboard plate (y-axis). The calculated R-squared value in this example is 0.983, establishing a good GOF.

In step 516 of FIG. 6, if there is a good fit, then the instrument outputs a dye matrix at step 518 of FIG. 6. A statistical good fit may occur, in R-squared analysis for example, when R-squared values are, for example, greater than or equal to 0.85 or RMSE values are, for example, less than or equal to 0.01, such as that illustrated in FIG. 9. The dye matrix can be prepared, for example, by processor 204 of computing system 200, and outputted to display 212.

In step 520 of FIG. 6, if there is a bad fit, then the instrument performs a local modeling at step 522 of FIG. 6. This can become necessary, for example, if the calculated $R^2$ value for a GOF check is less than 0.85, for example, and RMSE values are greater than 0.01, for example. The local modeling can be performed, for example, by processor 204, of computing system 200, by using the data from the dye presented wells for a specific dye to model for the remaining dye unpresented wells. The resulting model can be stored, for example, on memory 206 or storage device 210.

A local modeling method can include, for example, using the calibration factors from the surrounding dye presented wells for the same dye on the plate. For example, to determine the calibration factor value in a dye unpresented well for a specific dye, the local model can take the median value of all specific dye presented wells of the same dye that are within a 5×5 local window of surrounding wells or from the whole plate. That median value is determined until a full modeling of the plate is completed. The local modeling output can then replace the global modeling output.

At the conclusion of the local modeling, the dye matrix is sufficient such that the instrument outputs the dye matrix at step 518 of FIG. 6. This dye matrix serves as a profile of the fluorescence signature of each calibrated dye. After each run, the instrument receives data in the form of a raw spectra signal for each reading. The instrument determines the contribution of the fluorescent dyes used in each reaction by comparing the raw spectra to the pure spectra calibration data of the dye matrix. The instrument uses the calibration data collected from the dye standards (i.e., the dye matrix) to characterize and distinguish the individual contribution of each dye in the total fluorescence collected by the instrument.

In a first embodiment, a computer-implemented method for calibrating a fluorescent dye is provided, the method comprising imaging a sample holder, loaded into an instrument, at more than one channel, the sample holder comprising a plurality of reaction sites and more than one dye type, each dye occupying more than one reaction site; identifying a peak channel for each dye on the sample holder; normalizing each channel to the peak channel for each dye; and producing a dye matrix comprising a set of dye reference values.

In a second embodiment, the computer-implemented method of the first embodiment is provided, wherein the sample holder is a plate.

In a third embodiment, the computer-implemented method of the first and second embodiments is provided, wherein the plurality of reactions sites is a plurality of wells.

In a fourth embodiment, the computer-implemented method of any of the preceding embodiments is provided, wherein one dye occupies each well.

In a fifth embodiment, the computer-implemented method of any of the preceding embodiments is provided, wherein the dyes are distributed in a pattern along the reaction sites such that each dye occupies substantially the same number of reaction sites.

In a sixth embodiment, the computer-implemented method of any of the preceding embodiments is provided, wherein the dyes are distributed in a pattern along the reaction sites such that dyes occupying adjacent reaction sites are different.

In a seventh embodiment, the computer-implemented method of any of the preceding embodiments is provided, wherein the instrument is a biological analysis device.

In an eighth embodiment, the computer-implemented method of any of the preceding embodiments is provided, wherein the instrument is a PCR instrument.

In a ninth embodiment, the computer-implemented method of any of the preceding embodiments is provided, further comprising performing, for a given dye, a first model for reaction sites not occupied by the given dye.

In a tenth embodiment, the computer-implemented method of any of the preceding embodiments is provided, further comprising applying, for a given dye, a two-dimensional quadratic polynomial function as a first model for reaction sites not occupied by the given dye.

In an eleventh embodiment, the computer-implemented method of any of the ninth and tenth embodiments is provided, further comprising performing a goodness of fit check on the results of the first model.

In a twelfth embodiment, the computer-implemented method of any of the ninth and tenth embodiments is provided, further comprising performing an r-squared analysis or RMSE on the results of the first model.

In a thirteenth embodiment, the computer-implemented method of any of the ninth through twelfth embodiments is provided, further comprising performing, for a given dye, a second modeling for reaction sites not occupied by the given dye.

In a fourteenth embodiment, the computer-implemented method of any of the ninth through twelfth embodiments is provided, further comprising performing, for a given dye, a second modeling for reaction sites not occupied by the given dye when the goodness of fit of the first model fails a threshold.

In a fifteenth embodiment, the computer-implemented method of the twelfth embodiment is provided, further comprising performing, for a given dye, an r-squared or RMSE analysis for reaction sites not occupied by the given dye when the r-squared analysis of the first model fails a threshold.

In a sixteenth embodiment, the computer-implemented method of any of the fourteenth and fifteenth embodiments is provided, wherein the threshold of r-squared is 0.85 and the threshold of RMSE is 0.01.

In a seventeenth embodiment, the computer-implemented method of any of the preceding embodiments is provided, wherein the more than one dye is selected from the group consisting of FAM, VIC, ROX, SYBR, MP, ABY, JUN, NED, TAMRA, CY5, a custom dye and combinations thereof.

In an eighteenth embodiment, a non-transitory computer-readable storage medium encoded with instructions is provided, executable by a processor, for calibrating a fluorescent dye, the instructions comprising instructions for imaging a sample holder, loaded into an instrument, at more than one channel, the sample holder comprising a plurality of reaction sites and more than one dye type, each dye occupying more than one reaction site; identifying a peak channel for each dye on the sample holder; normalizing each channel to the peak channel for each dye; and producing a dye matrix comprising a set of dye reference values.

In a nineteenth embodiment, the non-transitory computer-readable storage medium of the eighteenth embodiment is provided, wherein the sample holder is a plate.

In a twentieth embodiment, the non-transitory computer-readable storage medium of the eighteenth and nineteenth embodiments is provided, wherein the plurality of reactions sites is a plurality of wells.

In a twenty first embodiment, the non-transitory computer-readable storage medium of any of the eighteenth through twentieth embodiments is provided, wherein one dye occupies each well.

In a twenty second embodiment, the non-transitory computer-readable storage medium of any of the eighteenth through twenty first embodiments is provided, wherein the dyes are distributed in a pattern along the reaction sites such that each dye occupies substantially the same number of reaction sites.

In a twenty third embodiment, the non-transitory computer-readable storage medium of any of the eighteenth through twenty second embodiments is provided, wherein the dyes are distributed in a pattern along the reaction sites such that dyes occupying adjacent reaction sites are different.

In a twenty fourth embodiment, the non-transitory computer-readable storage medium of any of the eighteenth through twenty third embodiments is provided, wherein the instrument is a biological analysis device.

In a twenty fifth embodiment, the non-transitory computer-readable storage medium of any of the eighteenth through twenty fourth embodiments is provided, wherein the instrument is a PCR instrument.

In a twenty sixth embodiment, the non-transitory computer-readable storage medium of any of the eighteenth through twenty fifth embodiments is provided, further comprising performing, for a given dye, a first model for reaction sites not occupied by the given dye.

In a twenty seventh embodiment, the non-transitory computer-readable storage medium of any of the eighteenth through twenty sixth embodiments is provided, further comprising applying, for a given dye, a two-dimensional quadratic polynomial function as a first model for reaction sites not occupied by the given dye.

In a twenty eighth embodiment, the non-transitory computer-readable storage medium of any of the twenty sixth and twenty seventh embodiments is provided, further comprising performing a goodness of fit check on the results of the first model.

In a twenty ninth embodiment, the non-transitory computer-readable storage medium of any of the twenty sixth and twenty seventh embodiments is provided, further comprising performing an r-squared analysis on the results of the first model.

In a thirtieth embodiment, the non-transitory computer-readable storage medium of any of the twenty sixth to twenty ninth embodiments is provided, further comprising performing, for a given dye, a second modeling for reaction sites not occupied by the given dye.

In a thirty first embodiment, the non-transitory computer-readable storage medium of any of the twenty sixth to twenty ninth embodiments is provided, further comprising performing, for a given dye, a second modeling for reaction sites not occupied by the given dye when the goodness of fit of the first model fails a threshold.

In a thirty second embodiment, the non-transitory computer-readable storage medium of any of the twenty sixth to twenty ninth embodiments is provided, further comprising performing, for a given dye, an r-squared analysis or RMSE for reaction sites not occupied by the given dye when the r-squared analysis of the first model fails a threshold.

In a thirty third embodiment, the non-transitory computer-readable storage medium of any of the thirty first to thirty second embodiments is provided, wherein the threshold of r-squared is 0.85 and the threshold of RMSE is 0.01.

In a thirty fourth embodiment, the non-transitory computer-readable storage medium of any of the eighteenth to thirty third embodiments is provided, wherein the more than one dye is selected from the group consisting of FAM, VIC, ROX, SYBR, MP, ABY, JUN, NED, TAMRA, CY5, a custom dye and combinations thereof.

In a thirty fifth embodiment, a system for calibrating a fluorescent dye is provided, the system comprising a processor; and a memory encoded with instructions, executable by the processor, the instructions for imaging a sample holder, loaded into an instrument, at more than one channel, the sample holder comprising a plurality of reaction sites and more than one dye type, each dye occupying more than one reaction site; identifying a peak channel for each dye on the sample holder; normalizing each channel to the peak channel for each dye; and producing a dye matrix comprising a set of dye reference values.

In a thirty sixth embodiment, the system of the thirty fifth embodiment is provided, wherein the sample holder is a plate.

In a thirty seventh embodiment, the system of any of the thirty fifth and thirty sixth embodiments is provided, wherein the plurality of reactions sites is a plurality of wells.

In a thirty eighth embodiment, the system of any of the thirty fifth to thirty seventh embodiments is provided, wherein one dye occupies each well.

In a thirty ninth embodiment, the system of any of the thirty fifth to thirty eighth embodiments is provided, wherein the dyes are distributed in a pattern along the reaction sites such that each dye occupies substantially the same number of reaction sites.

In a fortieth embodiment, the system of any of the thirty fifth to thirty ninth embodiments is provided, wherein the dyes are distributed in a pattern along the reaction sites such that dyes occupying adjacent reaction sites are different.

In a forty first embodiment, the system of any of the thirty fifth to fortieth embodiments is provided, wherein the instrument is a biological analysis device.

In a forty second embodiment, the system of any of the thirty fifth to forty first embodiments is provided, wherein the instrument is a PCR instrument.

In a forty third embodiment, the system of any of the thirty fifth to forty second embodiments is provided, further comprising performing, for a given dye, a first model for reaction sites not occupied by the given dye.

In a forty fourth embodiment, the system of any of the thirty fifth to forty second embodiments is provided, further comprising applying, for a given dye, a two-dimensional quadratic polynomial function as a first model for reaction sites not occupied by the given dye.

In a forty fifth embodiment, the system of any of the forty third to forty fourth embodiments is provided, further comprising performing a goodness of fit check on the results of the first model.

In a forty sixth embodiment, the system of any of the forty third to forty fourth embodiments is provided, further comprising performing an r-squared or RMSE analysis on the results of the first model.

In a forty seventh embodiment, the system of any of the forty third to forty sixth embodiments is provided, further comprising performing, for a given dye, a second modeling for reaction sites not occupied by the given dye.

In a forty eighth embodiment, the system of any of the forty third to forty sixth embodiments is provided, further comprising performing, for a given dye, a second modeling for reaction sites not occupied by the given dye when the goodness of fit of the first model fails a threshold.

In a forty ninth embodiment, the system of any of the forty third to forty sixth embodiments is provided, further comprising performing, for a given dye, an r-squared analysis for reaction sites not occupied by the given dye when the r-squared analysis of the first model fails a threshold.

In a fiftieth embodiment, the system of any of the forty eighth to forty ninth embodiments is provided, wherein the r-squared threshold is 0.85 and the RMSE threshold is 0.01.

In a fifty first embodiment, the system of any of the thirty fifth to fiftieth embodiments is provided, wherein the more than one dye is selected from the group consisting of FAM, VIC, ROX, SYBR, MP, ABY, JUN, NED, TAMRA, CY5, a custom dye and combinations thereof.

In a fifty second embodiment, a sample holder for calibrating fluorescent dyes is provided, the sample holder comprising a plurality of reaction sites, each of the plurality of reaction sites configured to accept a single dye, and wherein the sample holder is configured to accept more than one dye.

In a fifty third embodiment, the sample holder of the fifty second embodiment is provided, wherein the sample holder is a plate.

In a fifty fourth embodiment, the sample holder of any of the fifty second to fifty third embodiments is provided, wherein the plurality of reactions sites is a plurality of wells.

In a fifty fifth embodiment, the sample holder of any of the fifty second to fifty fourth embodiments is provided, wherein the dyes are distributed in a pattern along the reaction sites such that each dye of the more than one dye occupies substantially the same number of reaction sites as the other of the more than one dye.

In a fifty sixth embodiment, the sample holder of any of the fifty second to fifty fifth embodiments is provided, wherein the dyes are distributed in a pattern along the reaction sites such that dyes occupying adjacent reaction sites are different.

In a fifty seventh embodiment, the sample holder of any of the fifty second to fifty fifth embodiments is provided, wherein the dyes are distributed in a repeating alternating pattern along the reaction sites.

In a fifty eighth embodiment, the sample holder of any of the fifty second to fifty sixth embodiments is provided, wherein the distribution of the dyes forms a checkerboard pattern.

In a fifty ninth embodiment, the sample holder of any of the fifty second to fifty seventh embodiments is provided, wherein a single dye is distributed in each reaction site.

In a sixtieth embodiment, the computer-implemented method of any of the first to sixth embodiments is provided, wherein the dyes are distributed in a repeating alternating pattern along the reaction sites.

In a sixty first embodiment, the computer-implemented method of any of the first to sixth embodiments is provided, wherein the distribution of the dyes forms a checkerboard pattern.

In a sixty second embodiment, the non-transitory computer-readable storage medium of any of the eighteenth to twenty third embodiments is provided, wherein the dyes are distributed in a repeating alternating pattern along the reaction sites.

In a sixty third embodiment, the non-transitory computer-readable storage medium of any of the eighteenth to twenty third embodiments is provided, wherein the distribution of the dyes forms a checkerboard pattern.

In a sixty fourth embodiment, the system of any of the thirty fifth to fortieth embodiments is provided, wherein the dyes are distributed in a repeating alternating pattern along the reaction sites.

In a sixty fifth embodiment, the system of any of the thirty fifth to fortieth embodiments is provided, wherein the distribution of the dyes forms a checkerboard pattern.

In a sixty sixth embodiment, the computer-implemented method of any one the first to seventeenth embodiments is provided, wherein the sample holder comprises 3 dyes.

In a sixty seventh embodiment, the computer-implemented method of any one the first to seventeenth embodiments is provided, wherein the sample holder comprises 4 dyes.

In a sixty eighth embodiment, the non-transitory computer-readable storage medium of any one of claims eighteenth to thirty fourth embodiments is provided, wherein the sample holder comprises 3 dyes.

In a sixty ninth embodiment, the non-transitory computer-readable storage medium of any one of claims eighteenth to thirty fourth embodiments is provided, wherein the sample holder comprises 4 dyes.

In a seventieth embodiment, the system of any one of the thirty fifth to fifty first embodiments is provided, wherein the sample holder comprises 3 dyes.

In a seventy first embodiment, the system of any one of the thirty fifth to fifty first embodiments is provided, wherein the sample holder comprises 4 dyes.

In a seventy second embodiment, the sample holder of any one of the fifty second to fifty eighth embodiments is provided, wherein the sample holder is configured to accept 3 dyes.

In a seventy third embodiment, the sample holder of any one of the fifty second to fifty eighth embodiments is provided, wherein the sample holder is configured to accept 4 dyes.

In a seventy fourth embodiment, the sample holder of the fifty ninth embodiment is provided, further comprising 3 dyes.

In a seventy fifth embodiment, the sample holder of the fifty ninth embodiment is provided, further comprising 4 dyes.

Various embodiments of the present invention have been described above. It should be understood that these embodiments have been presented by way of example only, and not limitation. It will be understood by those skilled in the relevant art that various changes in form and detail of the embodiments described above may be made without departing from the spirit and scope of the present invention as defined in the claims. Thus, the breadth and scope of the present invention should not be limited by any of the above-described exemplary embodiments, but should be defined only in accordance with the following claims and their equivalents.

The invention claimed is:

1. A computer-implemented method for calibrating a fluorescent dye, the method comprising:
   imaging a sample holder, loaded into an instrument, at more than one channel, the sample holder comprising a plurality of reaction sites and a plurality of dyes comprising more than one dye type, each dye occupying more than one reaction site, wherein the plurality of dyes are distributed in a checkerboard pattern among the reaction sites;
   identifying a peak channel for each dye on the sample holder;
   normalizing each channel to the peak channel for each dye; and
   producing a dye matrix comprising a set of dye reference values.

2. The computer-implemented method of claim 1, wherein the dyes are distributed in a pattern along the reaction sites such that each dye occupies substantially the same number of reaction sites.

3. The computer-implemented method of claim 1, wherein the dyes are distributed in a pattern along the reaction sites such that dyes occupying adjacent reaction sites are different.

4. The computer-implemented method of claim 1, wherein the plurality of dyes are distributed in a repeating alternating pattern along the reaction sites.

5. The computer-implemented method of claim 1, further comprising:
   performing, for a given dye, a first modeling for reaction sites not occupied by the given dye.

6. The computer-implemented method of claim 5, further comprising:
performing a goodness of fit check on the results of the first modeling.

7. The computer-implemented method of claim 5, further comprising:
performing, for a given dye, a second modeling for reaction sites not occupied by the given dye.

8. A non-transitory computer-readable storage medium encoded with instructions, executable by a processor, for calibrating a fluorescent dye, the instructions comprising instructions for:
imaging a sample holder, loaded into an instrument, at more than one channel, the sample holder comprising a plurality of reaction sites and a plurality of dyes comprising more than one dye type, each dye occupying more than one reaction site, wherein the plurality of dyes are distributed in a checkerboard pattern among the reaction sites;
identifying a peak channel for each dye on the sample holder;
normalizing each channel to the peak channel for each dye; and
producing a dye matrix comprising a set of dye reference values.

9. The non-transitory computer-readable storage medium of claim 8, wherein the dyes are distributed in a pattern along the reaction sites such that each dye occupies substantially the same number of reaction sites.

10. The non-transitory computer-readable storage medium of claim 8, wherein the dyes are distributed in a pattern along the reaction sites such that dyes occupying adjacent reaction sites are different.

11. The non-transitory computer-readable storage medium of claim 8, wherein the plurality of dyes are distributed in a repeating alternating pattern along the reaction sites.

12. The non-transitory computer-readable storage medium of claim 8, further comprising:
performing, for a given dye, a first modeling for reaction sites not occupied by the given dye.

13. The non-transitory computer-readable storage medium of claim 12, further comprising:
performing, for a given dye, a second modeling for reaction sites not occupied by the given dye.

14. A system for calibrating a fluorescent dye, the system comprising:
a processor; and
a memory encoded with instructions, executable by the processor, the instructions for:
imaging a sample holder, loaded into an instrument, at more than one channel, the sample holder comprising a plurality of reaction sites and a plurality of dyes comprising more than one dye type, each dye occupying more than one reaction site, wherein the plurality of dyes are distributed in a checkerboard pattern among the reaction sites;
identifying a peak channel for each dye on the sample holder;
normalizing each channel to the peak channel for each dye; and
producing a dye matrix comprising a set of dye reference values.

15. The system of claim 14, wherein the dyes are distributed in a pattern along the reaction sites such that each dye occupies substantially the same number of reaction sites.

16. The system of claim 14, wherein the dyes are distributed in a pattern along the reaction sites such that dyes occupying adjacent reaction sites are different.

17. The system of claim 14, wherein the plurality of dyes are distributed in a repeating alternating pattern along the reaction sites.

18. The system of claim 14, further comprising:
performing, for a given dye, a first modeling for reaction sites not occupied by the given dye.

19. The system of claim 18, further comprising:
performing a goodness of fit check on the results of the first modeling.

20. The system of claim 18, further comprising:
performing, for a given dye, a second modeling for reaction sites not occupied by the given dye.

* * * * *